United States Patent [19]

Savin et al.

[11] Patent Number: 4,950,227
[45] Date of Patent: Aug. 21, 1990

[54] STENT DELIVERY SYSTEM
[75] Inventors: Michael A. Savin, Norwood; James E. Windheuser, Watertown; Richard A. Noddin, Holliston, all of Mass.
[73] Assignee: Boston Scientific Corporation, Watertown, Mass.
[21] Appl. No.: 267,575
[22] Filed: Nov. 7, 1988
[51] Int. Cl.⁵ .......................................... A61M 29/00
[52] U.S. Cl. ...................................... 604/8; 606/192; 623/1
[58] Field of Search ........... 128/341, 343, 344, 303 R; 604/8, 104, 96, 281

[56] References Cited

U.S. PATENT DOCUMENTS

| | | | |
|---|---|---|---|
| 4,553,545 | 11/1985 | Maass et al. | 128/341 |
| 4,580,568 | 4/1986 | Gianturco | 128/345 |
| 4,649,922 | 3/1987 | Wiktor | 128/344 |
| 4,655,771 | 4/1987 | Wallsten | 623/343 |
| 4,665,918 | 5/1987 | Garza et al. | 128/343 |
| 4,681,110 | 7/1987 | Wiktor | 128/343 |
| 4,732,152 | 3/1988 | Wallsten et al. | 128/343 |
| 4,733,665 | 3/1988 | Palmaz | 128/343 |
| 4,739,762 | 4/1988 | Palmaz | 128/343 |
| 4,762,128 | 8/1988 | Rosenbluth | 128/343 |

FOREIGN PATENT DOCUMENTS

WO83/03752 11/1983 PCT Int'l Appl. .

OTHER PUBLICATIONS

Palmaz et al., "Expandable Intraluminal Graft: A Preliminary Study," Radiology, 156: 73-77, (1985).
Wright et al., "Percutaneous Endovascular Stents: An Experimental Evaluation," Radiology, 156: 69-72, (1985).
Palmaz et al., "Expandable Intraluminal Vascular Graft: A Feasibility Study," Surgery, 99: 199-204, (1986).
Wallace et al., "Tracheobronchial Tree: Expandable Metallic Stents Used in Experimental and Clinical Applications," Radiology, 158: 309-312, (1986).
Palmaz et al., "Atherosclerotic Rabbit Aortas: Expandable Intraluminal Grafting," Radiology, 160: 723-726 (1986).
Charnsangavej et al., "Stenosis of the Vena Cava: Preliminary Assessment with Expandable Metallic Stents," Radiology, 161: 295-298, (1986).
Rosch et al., "Experimental Intrahepatic Portacaval Anastomosis: Use of Expandable Gianturco Stents," Radiology, 162: 481-485, (1987).
Sigwart et al., "Intravascular Stents to Prevent Occlusion and Restenosis After Transluminal Angioplasty," NEJM, 316: 701-706, (1987).
Schatz et al., "Balloon-Expandable Intracoronary Stents in the Adult Dog," Circulation, 76: 450-457, (1987).
Roubin et al., "Early and Late Results of Intracoronary Arterial Stenting After Coronary Angioplasty in Dogs," Circulation, 76: 891-897, (1987).
Zollikofer et al., "Endovascular Stenting of Veins and Grafts: Preliminary Clinical Experience," Radiology, 167: 707-712, (1988).

Primary Examiner—Robert A. Hafer
Assistant Examiner—Lynda M. Cofsky
Attorney, Agent, or Firm—Fish & Richardson

[57] ABSTRACT

A stent delivery system to facilitate introduction and placement of a stent, including a catheter having an expansible distal portion constructed and arranged for expanding the outer diameter of the catheter from a contracted state to an expanded state; a stent positioned around the distal portion of the catheter, having a contracted condition and being expansible to an expanded condition, and being sized in the contracted condition to closely surround the catheter in the contracted state, the stent having an end portion defining a margin lying over the expansible portion of the catheter; a sleeve in the region of the distal portion of the catheter positioned around the catheter having a first end fixed to the catheter and a second end defining a margin lying over the margin of the stent; the sleeve fixing the end of the stent on the catheter when the catheter is in the contracted state, the catheter and stent cooperatively constructed and arranged to cause expansion of the catheter from its contracted state to its expanded state to cause expansion of the stent, including the margin of the stent, from its contracted condition to its expanded condition, and therewith cause the margin of the sleeve to slide axially from over the margin of the stent thereby releasing the end of the stent from the catheter.

36 Claims, 3 Drawing Sheets

U.S. Patent   Aug. 21, 1990   Sheet 1 of 3   4,950,227
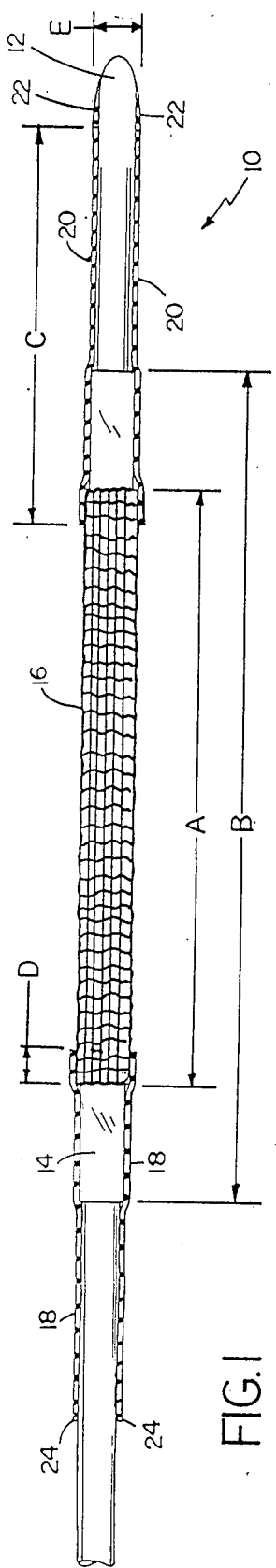
FIG.1
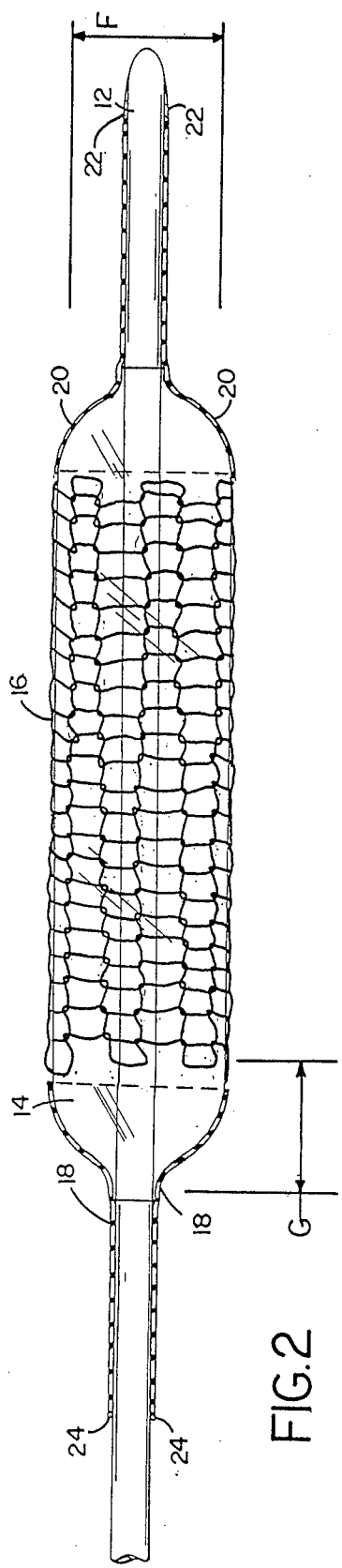
FIG.2
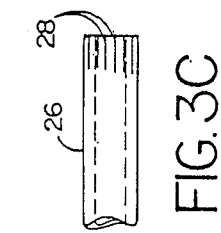
FIG.3C
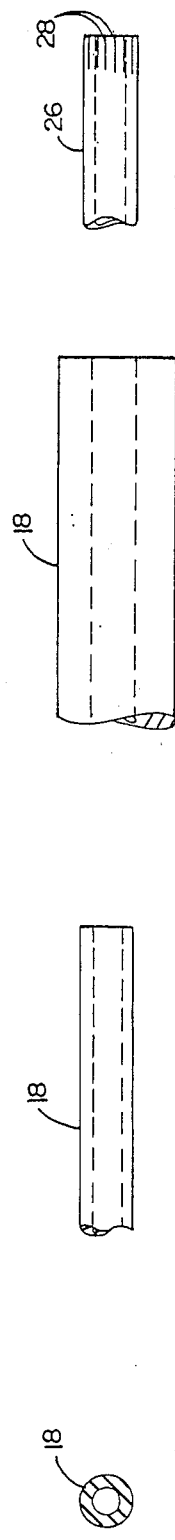
FIG.3A
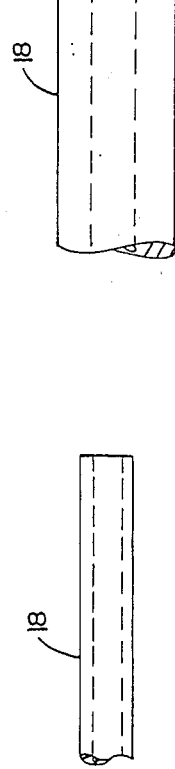
FIG.3
FIG.3B

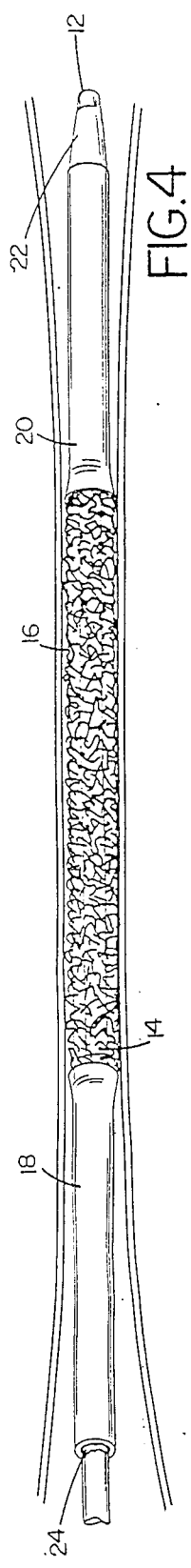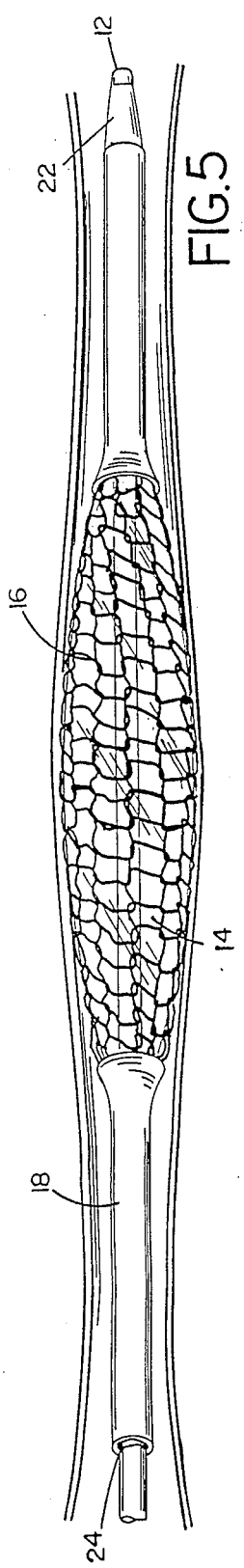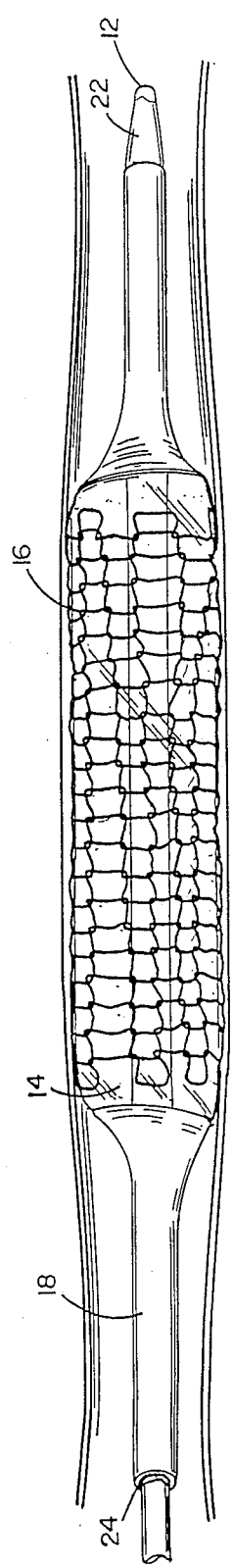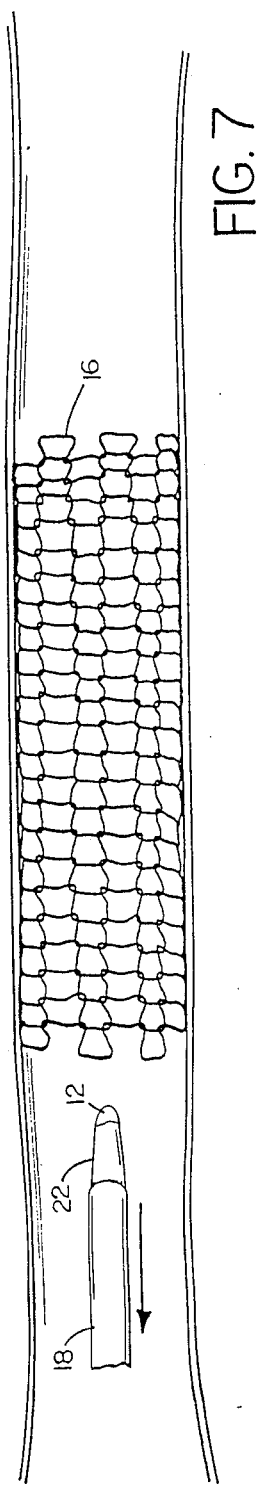

STENT DELIVERY SYSTEM

BACKGROUND OF THE INVENTION

This invention concerns apparatus suitable for delivery of stents to body cavities.

In general, stents are prosthetic devices which can be applied within a body cavity, for example, a blood vessel of the body of a living human, or in some other difficultly accessible place. The prosthesis is formed of a tubular body, the diameter of which can be decreased or increased. Stents are particularly useful for permanently widening a vessel which is either in a narrowed state, or internally supporting a vessel damaged by an aneurysm. Such stents are generally introduced to the body cavity by use of a catheter.

For example, Zollikofer et al., 167 Radiology 707 (1988), describes introduction of a self expanding stent (the Wallsten prosthesis) over a catheter. The stent is restrained to the catheter by a doubled over membrane, which is withdrawn when the stent is in the appropriate location by use of a sliding release device. Wallsten, U.S. Pat. No. 4,685,771, 1987, describes introduction of a prosthesis on a catheter, the prosthesis being held by gripping means. The prosthesis is expanded by pushing one of the gripping means toward the other so that a balloon-like shape is achieved. The quipping means are then released by use of a wire running the length of the catheter. Palmaz et al., 156 Radiology 73 (1985) and U.S. Pat. No. 4,733,665, describe introduction of a stent over a balloon catheter. The stent is held in place by oversized tapered leading and trailing retainers. These retainers appear to be an integral part of the balloon of the catheter.

SUMMARY OF THE INVENTION

In a first aspect, the invention features a stent delivery system including a catheter having an expansible distal portion constructed and arranged for expanding the outer diameter of the catheter from a contracted state to an expanded state; a stent positioned around the distal portion of the catheter, having a contracted condition and being expansible to an expanded condition, and being sized in the contracted condition to closely surround the catheter in the contracted state, the stent having an end portion defining a margin lying over the expansible portion of the catheter; a sleeve in the region of the distal portion of the catheter positioned around the catheter having a first end fixed to the catheter and a second end defining a margin lying over the margin of the stent; the sleeve fixing the end of the stent on the catheter when the catheter is in the contracted state, the catheter and stent cooperatively constructed and arranged to cause expansion of the catheter from its contracted state to its expanded state to cause expansion of the stent, including the margin of the stent, from its contracted condition to its expanded condition, and therewith cause the margin of the sleeve to slide axially from over the margin of the stent thereby releasing the end of the stent from the catheter.

In a second aspect, the invention features a catheter having an expansible distal portion constructed and arranged for expanding the outer diameter of the catheter from a contracted state to an expanded state; a stent positioned around the distal portion of the catheter, the stent having a contracted condition and being expansible to an expanded condition, and being sized in the contracted condition to closely surround the catheter in the contracted state, the stent having a first and second end portion defining a first and second margin both lying over the expansible portion of the catheter; a first and second sleeve in the region of the distal portion of the catheter positioned around the catheter, each having a first end laying over the catheter and a second end laying over a margin of the stent; each sleeve separately engaging the stent at the margins; the first and second sleeve fixing the ends of the stent on the catheter when the catheter is in the contracted state, the catheter and stent cooperatively constructed and arranged to cause expansion of the catheter from the contracted state to the expanded state to cause expansion of the stent, including the margins of the stent, from the contracted condition to the expanded condition, and therewith cause the margins of the first and second sleeve to slide axially from over the margins of the stent, thereby simultaneously releasing the ends of the stent from the catheter.

In preferred embodiments of the above aspects, the sleeve is elastomeric in a contracted state about the catheter, squeezing the margin of the stent thereagainst; the expansible distal portion is a balloon; the stent is expanded by the balloon mounted on a shaft of the catheter; the stent is formed of knitted material and the length of the stent does not significantly change when the stent is expanded; the stent delivery system further includes fixing means for holding the sleeve at a specific location on the catheter, most preferably the fixing means is a detent formed from adhesive; the stent delivery system further includes a hemostasis valve sheath, positioned through the skin and into a body cavity adapted to permit the catheter to be introduced through the sheath into the body cavity without injuring the cavity; the sleeve overlaps the stent at the margin for a maximum distance of 3 mm; the sleeve is formed from silicone; most preferably the sleeve is formed from an elastomer able to be expanded at least two times by internal pressure below those usable with a balloon angioplasty catheter, and formable into a thin walled tube, e.g., a pressure of about 3-17 atmospheres; the stent is able to expand elastically, super-elastically, and/or plastically in diameter; the sleeve fixes the stent at the distal end of the stent; the sleeve is formed in the shape of a cylinder; the sleeve has axially running regions of weakness where the sleeve contacts the stent; a lubricant is provided between the sleeve and the distal portion of the catheter; the stent has a lubricious coating; the sleeve is formed of radiopaque material, e.g., the sleeve includes a barium salt; the balloon of the catheter has a tapered diameter along all or a part of the section under the stent; and the stent is positioned with only a portion of the stent over the balloon.

In a second aspect, the invention features a method for fastening a stent to a catheter in a manner suitable for introduction, and later release, of the stent to a body cavity. The method includes the steps of (a) providing a catheter having an expansible distal portion constructed and arranged for expanding the outer diameter of the catheter, the distal portion having an expanded and a contracted state; (b) providing a stent having a contracted and an expanded condition; (c) sliding the stent axially over the catheter and about the distal portion; (d) providing a sleeve in an expanded form, the sleeve also having a contracted form; (e) sliding the expanded sleeve axially over the catheter and about a portion of the stent; (f) allowing the sleeve to contract about the catheter and the stent and thereby fix the stent to the catheter when the catheter and stent are in their contracted state or condition; the catheter and stent cooperating whereby the sleeve is released from the stent, but not from the catheter when the catheter is in its expanded state and the stent is in its expanded condition.

In preferred embodiments, the sleeve is formed of silicone and the expanded form of the sleeve is provided by soaking the sleeve in freon; the sleeve is allowed to contract by causing release of the freon from the sleeve; the sleeve is formed of polymeric material having the ability to expand more than two times its diameter and retract back to almost is original dimension; most preferably the material is chosen from latex, polyurethane, or polyether amide in water; the sleeve is held on the catheter by an adhesive detent; two sleeves are provided, one sleeve is fixed about the distal end of the stent, and the other sleeve about the proximal end; and the method further includes the step of providing a fixing means for holding the sleeve at a specific location on the catheter.

In a third aspect, the invention features a method for positioning a stent within a body cavity, including the steps of (a) providing the above described stent delivery system; (b) introducing the stent delivery system into the body cavity; (c) causing the distal portion of the catheter to expand and thereby simultaneously plastically deforming the stent and causing the margin to be released from the sleeve, at least partially contracting the catheter, and (d) removing the catheter and the sleeve from the body cavity by axially pulling the catheter from the body cavity.

This invention provides a simple and inexpensive method for fixing a stent to a balloon catheter, or its equivalent. The invention takes advantage of the expandability of silicone sleeves in freon and thus the tight grip that such sleeves apply to a stent on a catheter once the freon is released. Such sleeves are difficult to dislodge once applied but readily allow the stent to be expanded and released from the catheter when in a body cavity.

Other features and advantages of the invention will be apparent from the following description of the preferred embodiments thereof, and from the claims.

DESCRIPTION OF THE PREFERRED EMBODIMENTS

The drawings will first briefly be described.

Drawings

FIG. 1 is an isometric view, partially in longitudinal section, of a balloon catheter having a stent fixed to the catheter by a pair of retaining sleeves;

FIG. 2 is the catheter of FIG. 1 shown in an expanded state.

Figure 2A:
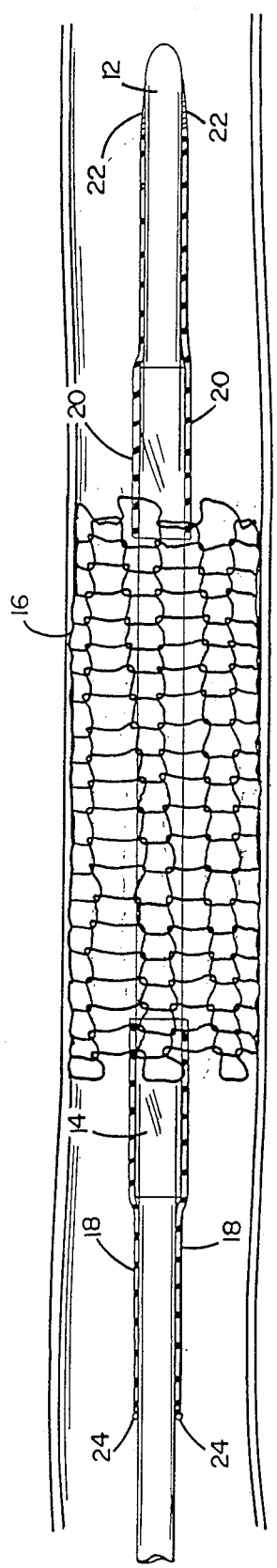
FIG. 2A is the catheter in a contracted state after being expanded.

FIG. 3 is a longitudinal section through a contracted retaining sleeve; FIG. 3A is a longitudinal section through an expanded retaining sleeve; FIG. 3B is a transverse section through a contracted retaining sleeve; and FIG. 3C is an alternative embodiment of a retaining sleeve.

FIGS. 4, 5, 6 and 7 are isometric views showing simultaneous expansion of a catheter balloon and stent, and the resulting release of the stent from a pair of retaining sleeves.

Structure

Referring to FIG. 1, stent delivery system 10 includes an Ultra-Thin ™ balloon catheter of length about 95 centimeters, and a diameter of about 5 French (0.066 inches). A balloon 14 of length B, about 7 centimeters, and wall thickness about 0.0005 inch, is fixed to catheter 12 by standard procedure. Balloon 14 is shown in its contracted state in FIG. 1. A stent 16 is fixed about balloon 14 by two overlying retaining sleeves 18, 20. Stent 16 is formed of tantalum of length A, between 1.5-15.0, for example, about 3 cm including 22-23 rows of loops, with 6 loops around the circumference. Stent 16 is formed of wire of 0.1 mm diameter (but can be from 0.04 to 0.2 mm diameter), with loops ranging from 1.5 mm, generally 2 mm in length. Stent 16 is radially compressed against balloon 14 with a final diameter E, about 9 French. Stent 16 has an expanded diameter F (FIG. 2), between 2-30 mm, generally about 8 mm. Sleeves 18, 20 are formed of silicone of length C, about 2 centimeters, and outer diameter about 0.065 inches, inner diameter 0.03 inches and wall thickness 0.0175 inches. Sleeves 18, 20 are axially fixed along catheter 12 by adhesive detents 22, 24 formed of a urethane bead (Conap St 115). Distal detent 22 is tapered to ensure that the catheter assembly does not damage or traumatize a body cavity as it is pushed into it. Thus, the tip of the catheter, the distal detent and distal sleeve 20 form a continuously tapered surface. Proximal sleeve detent 22 can also be tapered if desired. Further, sleeves 18, 20 may have tapered edges. The sleeves overlap stent 16 at each end, or margin, of stent 16, a distance D, about 3 mm.

Referring to FIG. 2, in its expanded state balloon 14 has a diameter of about 8 mm with a tapered portion from catheter 12 of length G, about 8 mm on each side of stent 16. Stent 16 is released from sleeves 18, 20 upon expansion of balloon 14, and, as shown, in FIG. 2A, the sleeves contract about balloon 14 when it is deflated. This deflation allows removal of balloon 14 and sleeves 18 and 20 with catheter 12, as the catheter is axially removed from a body cavity.

Referring to FIGS. 3, 3A and 3B, sleeve 18 in its contracted state has an outer diameter of about 0.065 inch and an inner diameter of 0.03 inch (FIGS. 3, FIG. 3B) and in its swollen state has an outer diameter of about 0.107 inch and an inner diameter of 0.050 inch (FIG. 3A). Sleeve 18 also expands approximately two fold in length when placed in liquid. If allowed to fully contact it will return to approximately its original dimensions. In its contracted state over a catheter it has an outer diameter of about 0.11 inch, thus exerting a strong circumferential force on the margin of the stent and on the balloon and catheter.

If required, a lubricating solution can be provided between balloon 14 and sleeve 18 and 20 to aid in release of stent 16 from the sleeves.

Method of Assembly

Referring to FIG. 1, in order to assemble stent delivery system 10, a stent 16 is cut to length A and catheter 12 and balloon 14 cleaned with standard detergent in an ultrasonic cleaner for 5 minutes. The balloon, catheter and stent are then rinsed in clean water and allowed to sit in a freon bath for 5 minutes. Silicone tubing for sleeves 18 and 20 is then cut to length C and soaked in a freon bath for 5 minutes, until the silicone tubing has swelled, as shown in FIG. 3A. Swelling of silicone by this treatment is generally described by Pope et al., U.S. Pat. No. 4,715,378.

A first silicone sleeve 18 is then pushed over the tip of catheter 12 and slid toward the proximal part of balloon 14; stent 16 is then immediately placed over balloon 14 and its distal end slipped under the first silicone sleeve 18. A second silicone sleeve 20 is then slid over the tip of catheter 12 and the distal end of stent 16 slipped under sleeve 20. Stent 16 and sleeves 18, 20 are then positioned, to overlap for a distance D, before the silicone sleeves are in their fully contracted states. Care is taken to ensure that the stent is not pulled lengthwise during this process. After about 10 minutes, silicone sleeves 18, 20 return to their original dimensions and hold stent 16 securely to balloon 14. Distal sleeve 20 may be slightly longer than the catheter and overlap its tip, thus it is trimmed as required. A bead of adhesive is then applied around the ends of each silicone sleeve in contact with catheter 12, to form tapered detents 22, 24 to prevent slippage of sleeves 18, 20 axially from stent 16. The whole system is allowed to cure for 24 hours and a standard Teflon ™ sheath of appropriate diameter (9 French inner diameter, 10 French outer diameter) is placed over stent 16 and balloon 14 for protection.

Use

Referring to FIGS. 4, 5, 6 and 7, stent delivery system 10 is encased as described above and inserted by standard technique into a body cavity of interest. At this point the stent is positioned (FIG. 4), as required by the physician, and balloon 14 expanded by standard technique (FIGS. 5 and 6). During this expansion, stent 16 is expanded to fill the body duct or cavity. Sleeves 18 and 20 release stent 16, at which point balloon 14 is deflated by standard technique, and catheter 12 and sleeves 18, 20 axially removed from the body cavity Stent 16 remains in place (FIG. 7).

Other Embodiments

Other embodiments are within the following claims. For example, stent 16 may be a self-expanding stent such that upon expansion of balloon 14 and release of stent 16 from sleeves 18 and 20, stent 16 automatically expands, e.g., elastically or is thermally induced (e.g., if the stent is formed of nitinol wire), to fill the body cavity. The stent may also be formed of non knitted material, such that its length A significantly decreases upon expansion, and thus, enhances its release from system 10. Any kind of stent may be delivered by this system, including plastically deformable or elastically deformable stents. These stents may be formed with different knitting parameters, wall thickness, material, loop size and may be superelastic. These stents may be covered with a membrane.

Adhesive detents 22, 24 may be replaced with fixed detents formed along catheter 12 during its manufacture, by standard technique. These detents act merely as stoppers to prevent axial dislodgement of sleeves 18, 20. Further, the sleeves 18, 20 may be affixed to the catheter with an underlying adhesive or overlaying shrink tube, a crimped metal ring, or a suture.

Sleeves 18, 20 can be formed of any other expandable substance, for example, polyurethane, latex or polyether amide. Generally, any material able to expand by more than two times in diameter and retract back to almost its original dimension is suitable. The material must also be able to be expanded at least two times by internal pressure below that usable with balloon angioplasty (about 3–17 atmospheres), and formable into a thin walled tube. Typical examples, include elastomers, such as natural rubber, thermoplastic elastomers, such as urethane, polyimides, and styrenes. Further, a hydrophilic polymer such as Palex 4011 (Atochem Inc.) is suitable. Only one sleeve 20 need be provided in a stent delivery system 10. Sleeve 20 prevents axial dislodgement of stent 16 as it passes along a body cavity. Sleeves 18, 20 may be formed as a cylinder, as shown in FIG. 3, or may be provided in an irregular form to allow easier release of stent 16 from system 10. Referring to FIG. 3C, scratch marks 28 may be provided, in order to enhance tearing and thus release of the silicone from the stent at the portion in contact with stent 16.

In order to enhance release of stent 16 after inflation and deflation of balloon 14, balloon 14 can be twisted about 20°. Similarly, in order to enhance positioning of stent 16 within a body cavity, sleeves 18, 20 may be formed of radiopaque material, such as barium sulfate, barium titanate, or any other metal salt which has an effect on X-rays.

Balloon 14 can include any means by which expansion of stent 16 is achieved, and thence release of stent 16 from sleeves 18, 20. This system can be used with any balloon catheter or other type of catheter with a shaft diameter from 4 to 15 French and balloon diameter in its expanded form of 2–30 millimeters. Balloon catheter 14 may be either non-tapered in the stent-engaging region, as shown in FIG. 2, or tapered, or stepped, as desired. This system may be used to deliver stents to, for example, coronary arteries, peripheral arteries (e.g., popliteal artery) and visceral arteries, veins, and to the biliary tree, the urinary tract, and the gastro-intestinal tract.

The above system may be used to expand just one end of a stent so that the stent is useful as a filter within the body cavity of interest. For such a use only one end of the stent is held over the balloon and thus expanded by the balloon.

We claim:

1. A stent delivery system comprising:

a catheter comprising an expansible distal portion constructed and arranged for expanding the outer diameter of said catheter from a contracted state to an expanded state, a stent positioned around said distal portion of said catheter, said stent having a contracted condition and being expansible to an expanded condition, and being sized in said contracted condition to closely surround said catheter in the contracted state, said stent having an end portion defining a margin lying over said expansible portion of said catheter, a sleeve in the region of said distal portion of said catheter positioned around said catheter, having a first end fixed to said catheter, and a second end defining a margin lying over said margin of said stent;

said sleeve fixing said end of said stent on said catheter when said catheter is in the contracted state, said catheter and stent cooperatively constructed and arranged to cause expansion of said catheter from said contracted state to said expanded state to cause expansion of said stent, including said margin of said stent, from said contracted condition to said expanded condition, and therewith cause said margin of said sleeve to slide relatively axially from over the margin of said stent, thereby releasing said end of the stent from said catheter.

2. The stent delivery system of claim 1, wherein said expansible distal portion comprises a balloon mounted on a shaft of the catheter.

3. The stent delivery system of claim 2, wherein said stent is expanded by expansion of said balloon.

4. The stent delivery system of claim 1 further comprising fixing means for holding said sleeve at a specific location on said catheter.

5. The stent delivery system of claim 4, said fixing means being a detent formed from adhesive.

6. The stent delivery system of claim 1, further comprising a hemostasis valve sheath, positioned through the skin into a body cavity, adapted to permit said catheter to be introduced through said sheath into said body cavity without injuring said cavity.

7. The stent delivery system of claim 1, wherein said sleeve overlaps said stent at said margin for a maximum distance of 3 mm.

8. The stent delivery system of claim 1, said sleeve being formed from silicone.

9. The stent delivery system of claim 1, said sleeve being formed from any elastomer able to be expanded at least two times by internal pressure below that usable with a balloon angioplasty catheter, and formable into a thin-walled tube.

10. The stent delivery system of claim 9, said pressure being between about 3–17 atmospheres.

11. The stent delivery system of claim 1, said stent being able to expand elastically in diameter.

12. The stent delivery system of claim 1, said stent being able to expand plastically in diameter.

13. The stent delivery system of claim 1, said end of said stent being a distal end, wherein said sleeve fixes said stent at the distal end of said stent.

14. The stent delivery system of claim 1, said sleeve being formed in the shape of a cylinder.

15. The stent delivery system of claim 1, said sleeve having axially running regions of weakness where said sleeve contacts said stent.

16. The stent delivery system of claim 1, wherein a lubricant is provided between said sleeve and said catheter.

17. The stent delivery system of claim 1, said stent having a lubricious or hydrophilic coating.

18. The stent delivery system of claim 1, said sleeve being formed of radiopaque material.

19. The stent delivery system of claim 18, said sleeve comprising a barium salt.

20. The stent delivery system of claim 1, said stent being able to expand superelastically in diameter.

21. A stent delivery system comprising:
a catheter comprising an expansible distal portion constructed and arranged for expanding the outer diameter of said catheter from a contracted state to an expanded state,
a stent positioned around said distal portion of said catheter, said stent having a contracted condition and being expansible to an expanded condition, and being sized in said contracted condition to closely surround said catheter in the contracted state, said stent having a first and second end portion defining a first and second margin lying over said expansible portion of said catheter,
a first and second sleeve in the region of said distal portion of said catheter positioned around said catheter, each having a first end fixed to said catheter and a second end defining a margin lying over a said margin of said stent,
said first sleeve and said second sleeve separately engaging said stent at said first margin and said second margin respectively;
said first and second sleeve fixing said ends of said stent on said catheter when said catheter is in the contracted state, said catheter and stent cooperatively constructed or arranged to cause expansion of said catheter from said contracted state to said expanded state to cause expansion of said stent, including said first and second margin of said stent, from said contracted condition to said expanded condition, and therewith cause said first and second margins of said sleeve to slide relatively axially from over the margins of said first and second stent, thereby simultaneously releasing said ends of the stent from said catheter.

22. The stent delivery system of claim 1 or 21 wherein a said sleeve is elastomeric in a contracted state about said catheter, squeezing the margin of said stent thereagainst.

23. The stent delivery system of claim 22, said balloon having a tapered diameter along all or part of the section under the stent.

24. The stent delivery system of claim 22, wherein only a portion of the stent is positioned over said balloon.

25. The stent delivery system of claim 22, said balloon having a tapered diameter along all of the section under the stent.

26. The stent delivery system of claim 1 or 21 wherein said stent is formed of knitted material and the length of said stent does not significantly change when said stent is expanded.

27. The stent delivery system of claim 1 or 21 wherein said stent is formed of material that enables the stent to decrease in length when said stent is expanded.

28. A method for fastening a stent to a catheter in a manner suitable for facilitating introduction, and later release, of said stent into a body cavity, comprising the steps of:
(a) providing a catheter having an expansible distal portion constructed and arranged for expanding the outer diameter of said catheter, said distal portion an expanded and a contracted state;
(b) providing a stent having an expanded and a contracted condition;
(c) sliding said stent axially over said catheter in the contracted state and about said distal
(d) providing a sleeve in an expanded form, said sleeve also having a contracted form;
(e) sliding said expanded sleeve axially over said catheter and about a portion of said stent; and
(f) allowing said sleeve to contract about said catheter and said stent and thereby fix said stent to said catheter when said catheter and said stent are in their contracted state or condition; said catheter and stent cooperating whereby said sleeve is released from said stent when said catheter is in its expanded state and said stent is in its expanded condition.

29. The method of claim 28, wherein said sleeve is formed of silicone and said expanded form of said sleeve is provided by soaking said sleeve in freon.

30. The method of claim 29 wherein said sleeve is allowed to contract by causing release of said freon from said sleeve.

31. The method of claim 28, wherein said sleeve is formed of a polymeric material that has the ability to expand more than two times in diameter and retract back to almost its original dimension.

32. The method of claim 31 wherein said material is chosen from latex, polyurethane, or polyether amide in water.

33. The method of claim 31 wherein said sleeve is held on the catheter by an adhesive detent.

34. The method of claim 28 wherein two said sleeves are provided; one said sleeve is fixed about a distal end of said stent and the other said sleeve about a proximal end of said stent.

35. The method of claim 28 further comprising the step of providing a fixing means for holding said sleeve at a specific location on said catheter.

36. A method for positioning a stent within a body cavity, comprising the steps of:
 (a) providing the stent delivery system of claim 1;
 (b) introducing said stent delivery system into said body cavity;
 (c) causing said distal portion of said catheter to expand and thereby simultaneously plastically deforming said stent and causing said margin to be released from said sleeve;
 (d) at least partially contracting said catheter; and
 (e) removing said catheter and said sleeve from said body cavity by axially pulling said catheter from the body cavity.

* * * * *

UNITED STATES PATENT AND TRADEMARK OFFICE
CERTIFICATE OF CORRECTION

PATENT NO. : 4,950,227

DATED : August 21, 1990

INVENTOR(S) : Savin et al.

It is certified that error appears in the above-identified patent and that said Letters Patent is hereby corrected as shown below:

Col. 1, line 18; insert a hyphen between "self expanding"
line 20; insert a hyphen between "doubled over"
line 27; "quipping" should be -- gripping --.

Col. 2, line 41; insert a hyphen between "thin walled".

Col. 3, line 24; insert a hyphen between "above described".

Col. 4, line 16; change "1.5" mm to -- 1-5 mm --.

Col. 5, line 44; insert a hyphen between "thermally induced".
line 46; insert a hyphen between "non knitted".

Col. 8, line 22; delete "all or" after "along"
line 48; insert -- portion;-- after "distal".

Signed and Sealed this

Twenty-eighth Day of April, 1992

Attest:

HARRY F. MANBECK, JR.

Attesting Officer

Commissioner of Patents and Trademarks